United States Patent
Takamura et al.

[11] Patent Number: 5,876,326
[45] Date of Patent: *Mar. 2, 1999

[54] ELECTRONIC ENDOSCOPE WITH GROUNDED SPIRALLY-WOUND LEAD WIRES

[75] Inventors: Koji Takamura, Hachioji; Takahiro Kishi, Machida; Hisao Yabe; Koji Yamaya, both of Hachioji; Masaaki Nakazawa, Hino; Hideo Ito, Akishima; Hiroshi Ishii, Hachioji, all of Japan

[73] Assignee: Olympus Optical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 579,148

[22] Filed: Dec. 27, 1995

[30] Foreign Application Priority Data

Mar. 10, 1995 [JP] Japan ................................. 7-051153
Mar. 20, 1995 [JP] Japan ................................. 7-061049
Mar. 22, 1995 [JP] Japan ................................. 7-062890

[51] Int. Cl.$^6$ ................................................. A61B 1/05
[52] U.S. Cl. ..................... 600/110; 600/132; 600/178
[58] Field of Search ................................. 600/109, 110, 600/132, 134, 178; 128/908; 348/65, 71, 74, 75; 333/211, 206, 243, 244; 174/106 R, 108

[56] References Cited

U.S. PATENT DOCUMENTS

| | | |
|---|---|---|
| 3,191,132 | 6/1965 | Mayer . |
| 3,573,676 | 4/1971 | Mayer ................................. 333/243 |
| 4,077,022 | 2/1978 | Pitts, Jr. ............................ 174/106 R |
| 4,250,351 | 2/1981 | Bridges ............................. 174/106 R |
| 4,642,417 | 2/1987 | Ruthrof et al. .................... 174/106 R |
| 4,861,945 | 8/1989 | Buck et al. ............................ 333/243 |
| 4,879,992 | 11/1989 | Nishigaki et al. ..................... 600/110 |
| 4,974,075 | 11/1990 | Nakajima . |
| 5,454,366 | 10/1995 | Ito et al. ............................... 600/109 |
| 5,543,831 | 8/1996 | Tsuji et al. .............................. 348/65 |
| 5,569,158 | 10/1996 | Suzuki et al. ......................... 600/110 |

FOREIGN PATENT DOCUMENTS

| | | |
|---|---|---|
| 4-183432 | 6/1992 | Japan . |
| 6-142039 | 5/1994 | Japan . |
| 6142039 | 5/1994 | Japan . |
| WO 92/06520 | 4/1992 | WIPO . |

*Primary Examiner*—John P. Leubecker
*Attorney, Agent, or Firm*—Armstrong, Westerman, Hattori, McLeland & Naughton

[57] ABSTRACT

An electronic endoscope apparatus provided with an electronic endoscope having arranged thereon a solid-state image pickup element at an insertion portion, and external devices such as a light source device for supplying an illumination light to the electronic endoscope, a video processor for processing an electrical signal transmitted from the solid-state image pickup element of the electronic endoscope to produce a video signal. An electrical connection portion for electrically connecting the electronic endoscope and the video processor is provided at a connector portion which is provided at an end of a universal cord which connects the electronic endoscope and the light source device. An electromagnetic interference countermeasure member is provided which covers at least one of the connector portion, the universal cord and the external devices. A dual shield around a signal line is also provided which includes spirally-wound lead wires having different diameters and ends connected to video ground.

9 Claims, 13 Drawing Sheets

ELECTRONIC ENDOSCOPE WITH GROUNDED SPIRALLY-WOUND LEAD WIRES

BACKGROUND OF THE INVENTION

1. Field of the Invention

The present invention relates to an electronic endoscope apparatus for reducing radiation of undesirable noise from an electronic endoscope.

2. Description of the Related Art

Generally, an electronic endoscope is arranged as follows. That is, a solid-state image pickup element is arranged at a forward end of the electronic endoscope. An image pickup cable extends through a circuit substrate and electronic portions which are connected to the solid-state image pickup element. The image pickup cable is adapted to be inserted into and to pass through the interior of an insertion portion, an operation portion and a universal cord of the endoscope, and is connected to a connector portion which is provided at an end of the universal cord.

Further, the electronic endoscope is connected to a processor, a light source device, a monitor and possibly other accessory equipment and is used as an electronic endoscope apparatus. A plurality of operation switches, which are arranged at the operation portion of the electronic endoscope apparatus, make it possible to provide a stationary image, changeover of light modulation and control of external pieces of equipment. Within a universal cord, switch cables which extend from the operation switches are inserted and pass therethrough and are connected to the connector portion.

On one hand, in recent years, also with respect to electrical equipment devices which are used within a hospital, it has become more desirable to conduct electromagnetic compatibility ("EMC") countermeasures. For this reason, with respect to the above-described electronic endoscope apparatus, EMC has been mentioned as a technologically important matter.

Accordingly, in order to prevent an electrical signal which is used in the electronic endoscope apparatus from being radiated external of the apparatus to cause malfunction of other pieces of electronic equipment, or to prevent noises which are radiated from other pieces of electronic equipment from mixing and interfering within the electronic endoscope apparatus to reduce the image quality of an endoscope image, thus causing malfunction of a control signal, the connector portion which is provided with many electrical contacts particularly requires increased shielding and protection from radiated noise.

For this reason, an arrangement in which a mechanism is provided which shields the connector portion with a metal member, and an arrangement whose construction is such that an electromagnetic absorber member is provided between the electronic endoscope and a patient circuit are disclosed in Japanese Patent Unexamined Publication No. HEI 4-183432 (183432/1992). Moreover, disclosed in Japanese Patent Unexamined Publication No. HEI 6-142039 (142039/1994) is an arrangement in which a metal blade is provided within the universal cord, which has one end thereof conducted to a connector receipt, to thereby form electromagnetic screening or shielding means or electromagnetic interference countermeasure means.

However, there is the following problem. That is, for the construction in which the metal member is used to shield the connection portion, as described above, or for the construction in which the electromagnetic absorber member is provided between the endoscope and the patient circuit, as disclosed in Japanese Patent Unexamined Publication No. HEI 4-183432, or the like, the connector portion is large and bulky and is excessively heavy, thereby reducing convenience and ease of use.

Furthermore, in order to incorporate the electromagnetic interference countermeasure means into the universal cord, not only are many man-hours and many steps required, but also convenience in use is deteriorated. If the electromagnetic interference countermeasure means is once incorporated into the electronic endoscope, an electronic endoscope in which the electromagnetic interference countermeasure has been halted exists regardless of whether or not the EMC countermeasures are necessary. For this reason, even also in a case where there is no interference if the conventional or prior art electronic endoscope is used, an electronic endoscope which has been halted in the electromagnetic interference countermeasure must be used, and a user is not given a chance of selection. For this reason, it is desirable that the EMC countermeasures can simply be conducted or performed to the existing electronic endoscope, as the occasion demands, when the existing electronic endoscope is used in combination with, for example, an equipment which is likely to generate the undesirable noise.

SUMMARY OF THE INVENTION

An object of the present invention is to provide an electronic endoscope apparatus in which EMC countermeasures which reduce radiation and mixture of unnecessary radiative noises are conducted, which is small in size, which is light in weight and which is convenient to use.

Another object of the present invention is to provide an electronic endoscope apparatus in which the use under a state in which sufficient reduction of radiation and mixture of unnecessary radiative noises can be selected in accordance with a given situation or set of circumstances.

Another object of the present invention is to provide an electronic endoscope apparatus in which EMC countermeasures can be formed easily and at low cost.

Briefly, an electronic endoscope apparatus according to the present invention is provided with an electronic endoscope having a solid-state image pickup element arranged in an insertion portion, and external devices, such as a light source device for supplying an illumination light to the electronic endoscope, a video processor for processing an electrical signal which is transmitted from the solid-state image pickup element of the electronic endoscope to provide a video signal. The electronic endoscope apparatus is arranged so as to be provided with an electrical connection portion electrically connecting the electronic endoscope and the video processor to each other at a connector portion which is provided at an end of a universal cord which connects the electronic endoscope and the light source device to each other, and in which at least one of the connector portion, the universal cord and at least one of the external devices is covered with an electromagnetic interference countermeasure member.

BRIEF DESCRIPTION OF THE DRAWINGS

FIG. 1 is an explanatory view showing a schematic arrangement of an electronic endoscope apparatus; and FIG. 2 is a perspective view describing a connector portion which includes an electromagnetic shielding cover as an electromagnetic interference countermeasure member.

FIG. 3 is a perspective view showing another arrangement of the electromagnetic shielding cover;

FIG. 4A is a view showing an engagement state of a developable portion of the electromagnetic shielding cover; and FIG. 4B is a view describing an arrangement of the developable portion of the electromagnetic shielding cover.

FIG. 5 is a perspective view showing another arrangement of the electromagnetic shielding cover;

FIG. 6A is a view showing a first shielding cover of the electromagnetic shielding cover;

FIG. 6B is a view showing a second shielding cover of the electromagnetic shielding cover; and FIG. 6C is a view showing an engagement state between the first shielding cover and the second shielding cover.

FIG. 14 is a cross-sectional view describing an arrangement of an electronic endoscope;

FIG. 15 is a front elevational view of the electronic endoscope from a forward end thereof; and FIG. 16 is a cross-sectional view describing a structure of a flexible pipe portion.

FIG. 17 is a cross-sectional view describing an arrangement of an electronic endoscope; and FIG. 18 is a cross-sectional view describing a structure of a flexible pipe portion.

FIG. 19 is a view showing an arrangement of an electronic endoscope apparatus;

FIG. 20 is an explanatory view showing a connection portion between a signal cable and an operation portion;

FIG. 21 is a perspective view snowing an internal arrangement of the signal cable, FIG. 22 is a perspective view showing an arrangement of a first electromagnetic absorber which is mounted to the signal cable:

FIG. 23 is a perspective view showing an arrangement of a second electromagnetic absorber which is mounted to the signal cable; and FIG. 24 is a view showing the entire electronic endoscope apparatus which has the signal cable to which the electromagnetic absorbers are mounted.

FIG. 25 is a perspective view showing an internal arrangement of a signal cable; and FIG. 26 is a graph describing the relationship between a diameter of the signal cable thereof and frequency.

DETAILED DESCRIPTION OF THE PREFERRED EMBODIMENTS

Various embodiments according to the present invention will hereunder be described with reference to the accompanying drawings.

First, electromagnetic interference countermeasures of a connector portion which requires shielding, strengthening or reinforcement will be described.

A first embodiment of the present invention will be described with reference to FIGS. 1 and 2.

Figure 1:
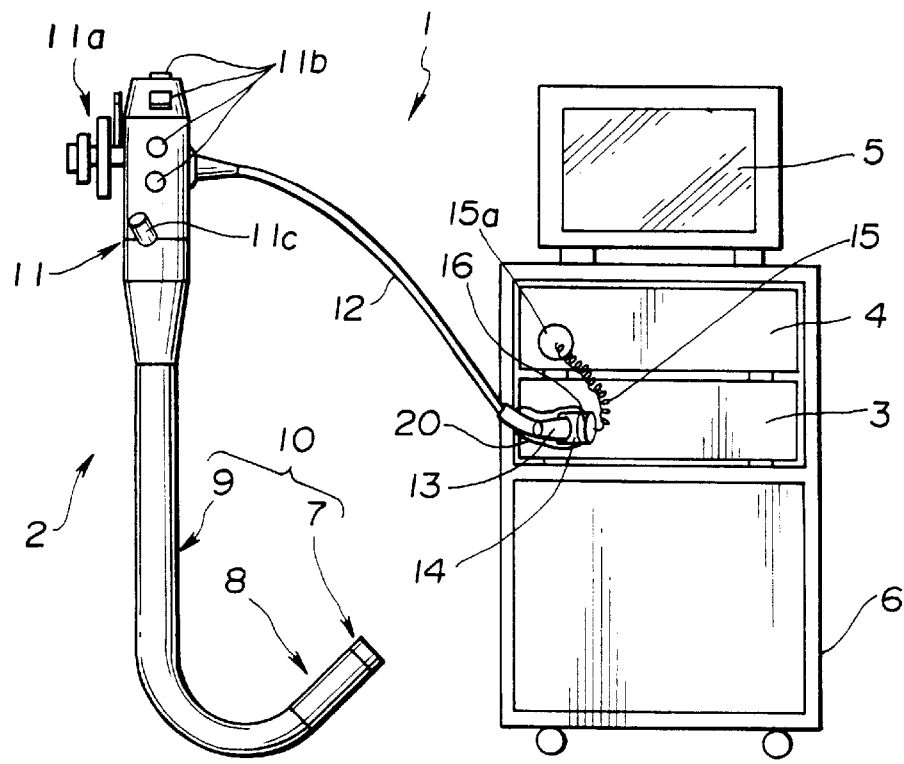
FIGS. 1 and 2 are views describing a first preferred exemplary embodiment of the present invention, where

As shown in FIG. 1, an electronic endoscope apparatus 1 principally comprises an electronic endoscope 2 having built therein a solid-state image pickup element to be described later, such as a CCD, and a cart 6 which stores therein a light source device 3 and a video processor 4 and which has an upper face portion thereof on which a television monitor 5 rests, at the side of a forward end of an insertion portion.

The electronic endoscope 2 connects a forward-end forming portion 7 having an image pickup portion on which a solid-state image pickup element is arranged, a curvature portion 8 having a plurality of curvature pieces and an elastic pipe portion 9 having elasticity, to form an elongated insertion portion 10. The insertion portion 10 has an end portion thereof on the side of hand thereof to which an operation portion 11 is connected. Operation portion 11 has a curvature operation knob 11a for curvedly operating the curvature portion 8, buttons 11b for indicating gas supply, water supply and the like, an insertion port 11c through which a treatment tool is inserted into a treatment-tool channel (not shown) within the electronic endoscope 2. From the side of the operation portion 11, a universal cord 12 extends through which a gas supply pipe, a water supply pipe, a suction pipe, a light guide, and a plurality of signal cables pass. The universal cord 12 has a distal end thereof on which a connector portion 13 which is detachable to the light source device 3 is provided. The connector portion 13 has an armor member thereof which is formed by thermoplastic resin such as polysulfone, denaturated PPO, polyetherimide or the like, principally for the purpose of reducing the weight thereof.

Figure 2:
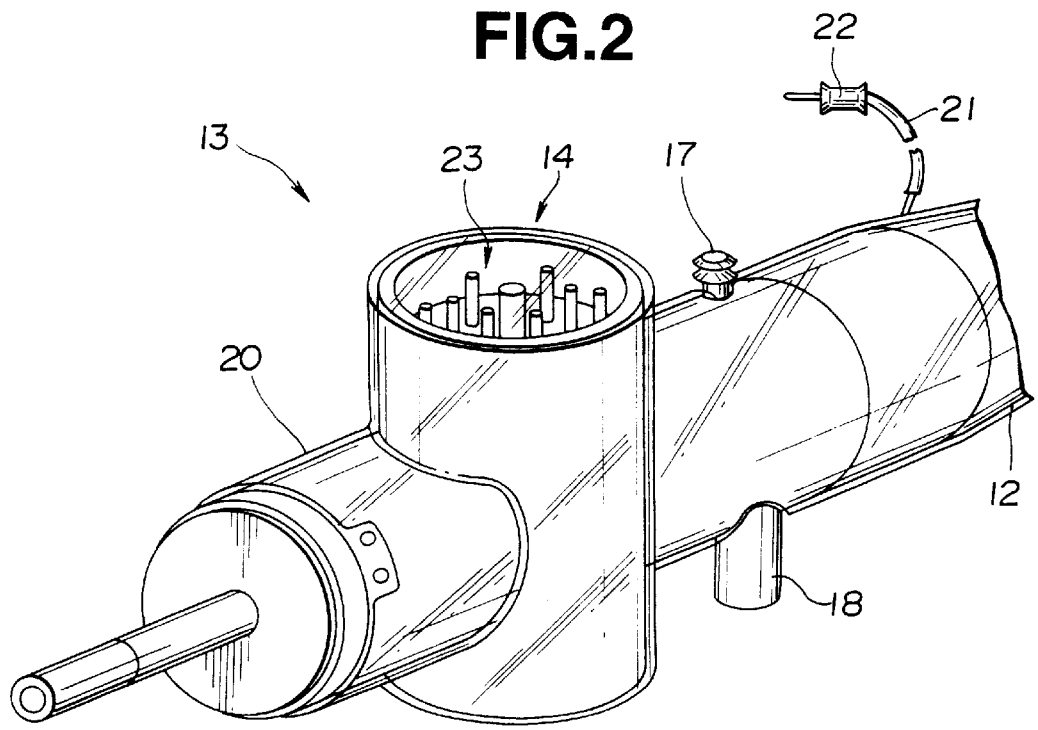

As shown in FIG. 2, an electrical connector portion 14 is provided on the side of the connector portion 13. To the electrical connector portion 14, an electrical-cord connector 16 of an electrical cord 15 is detachably connected which is provided with a connector 15a which in turn is detachably mounted to the video processor 4.

An electromagnetic shielding cover 20 which covers the entire connector portion is covered on the connector portion 13. The electromagnetic shielding cover 20 is a resin sheet which is formed by polyester, polyurethane or the like containing an electromagnetic absorber such as, for example, ferrite, or an arrangement in which a metal thin wire, such as stainless steel, is wound to form sheet.

Whenever the connector portion 13 is covered with the electromagnetic shielding cover 20 in which the metal thin wire is wound so as to be formed into a sheet, a terminal 22 which is provided at a forward end of a ground wire or line 21 which is electrically mounted on the electromagnetic shielding cover 20 by solder is connected to a reference electrical potential of the light source device 3, or is grounded through the light source device 3.

In connection with the above, whenever a resin sheet containing the electromagnetic absorber is used as the electromagnetic shielding cover 20, it is unnecessary to provide the ground line 21 and the terminal 22. Moreover, the reference numeral 17 in FIG. 2 is a suction base. The reference numeral 18 is a gas-supply.water-supply base, and the reference numeral 23 is a group of contact pins which are connected to the electrical cord 15.

In this manner, the connector portion is covered with the resin sheet containing the electromagnetic absorber, such as ferrite, or with the electromagnetic shielding cover in the form of the sheet in which the metal thin wire, such as stainless steel, is wound, whereby it is possible to provide the electronic endoscope apparatus in which the EMC countermeasures capable of executing the electromagnetic shielding which reduces radiation and the mixing of the radiative noises are conducted without use of an overly-large or extra heavy connector portion, regardless of the material and construction forming the connector portion.

A second embodiment of the present invention will be described with reference to FIGS. 3 and 4.

Figure 3:
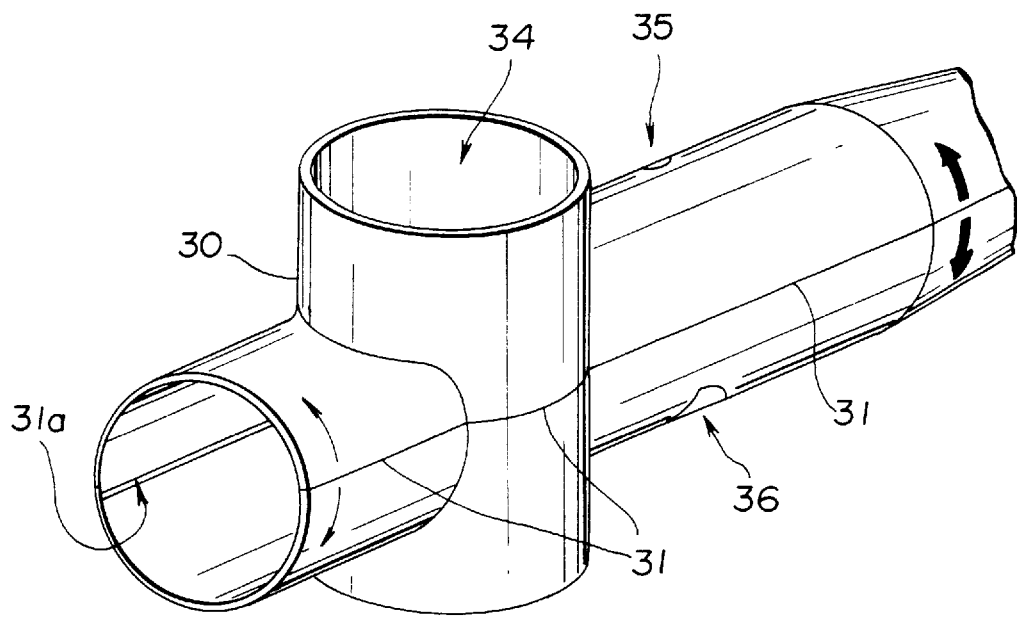
FIGS. 3 and 4A–B are explanatory views describing a second embodiment according to the present invention, where

As shown in FIG. 3, an electromagnetic shielding cover 30 of the second embodiment is formed into a elongatable thin plate form, in contrast to the fact that the electromagnetic shielding cover 20 in the first embodiment is in the form of a sheet. Specifically, the electromagnetic shielding cover 30 is a cover in which an electromagnetic absorber, such as ferrite, or metal powder, such as aluminum or stainless steel, is mixed into a resin material, such as polypropylene, which has elasticity, and is formed. A development portion 31 is so formed as to be elongatable in a direction indicated by arrows in FIG. 3.

Figure 4A:
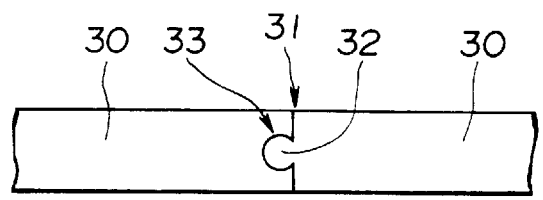

As shown in FIG. 4A, a projection 32 is formed on the side of one end face of the development portion 31, and a recess 33 which is engaged with the projection 32 is formed on the side of the other end face. Specifically, engagement between the projection 32 and the recess 33 which are formed in the end faces of the elongatable portion 31 is detached whereby the electromagnetic shielding cover 30 is detachable with respect to the connector portion 13. In this connection, reference numeral 34 shows an electrical-connector opening, reference numeral 35 shows a suction base opening, and reference numeral 36 is a gas-supply.water-supply base opening.

In this manner, the electromagnetic shielding cover is formed by a resin material having the ability to flex or bend, and is elongatable in a longitudinal direction, whereby it is possible to provide an electromagnetic shielding cover which is easily detachable with respect to the connector portion. Thus, the mountability or operability of the electromagnetic shielding cover to the connector portion is considerably improved. The other functions and advantages are similar to those of the first embodiment.

Figure 4B:
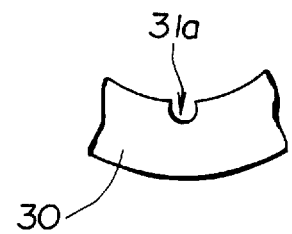

In connection with the above, a hinge portion 31a is provided at a position which is opposed to the elongatable portion 31, as shown in FIG. 4B, whereby not only the development of the electromagnetic shielding cover 30 is smoother, but also the durability thereof can be improved.

A third embodiment of the present invention will be described with reference to FIGS. 5 and 6.

Figure 5:
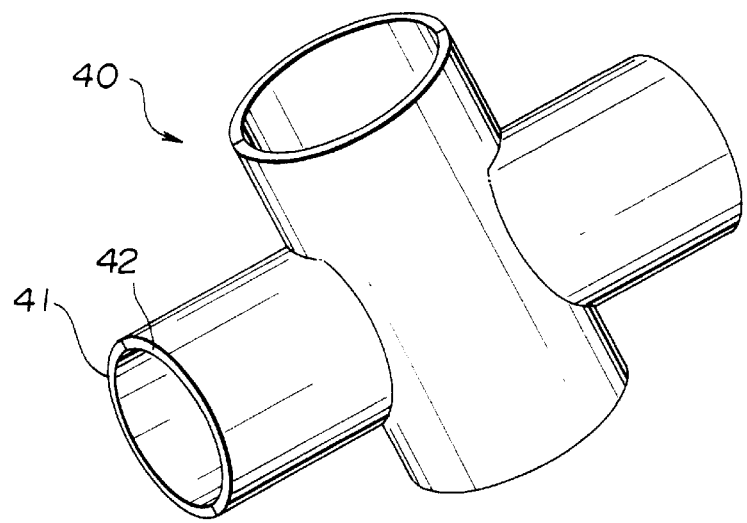
FIGS. 5 and 6A–C are views describing a third embodiment according to the present invention, where
Figure 6A:
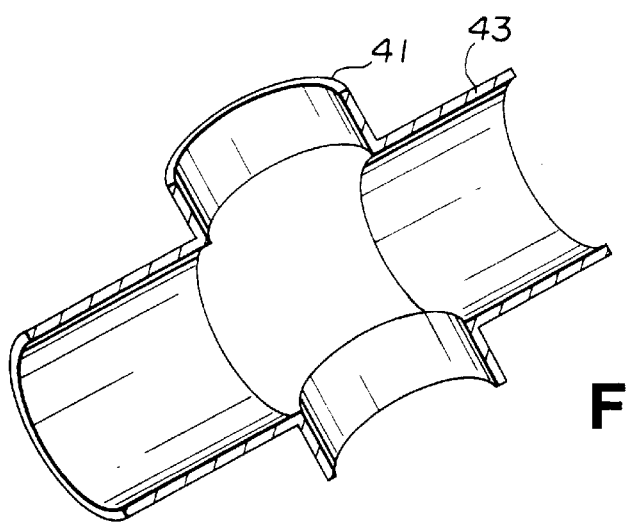
Figure 6C:
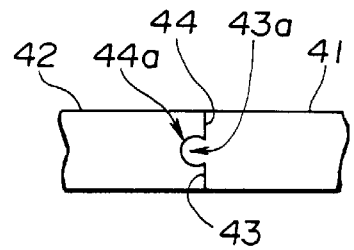
Figure 6B:
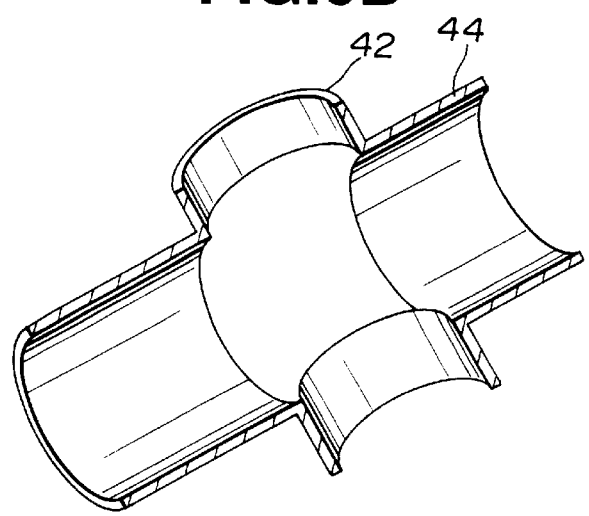

As shown in FIG. 5, an electromagnetic shielding cover 40 in the third embodiment is arranged so as to be able to be divided into a first shielding cover 41 and a second shielding cover 42, as shown in FIGS. 6A and 6B. The electromagnetic first shielding cover 41 and the second shielding cover 42 are formed such that an electromagnetic absorbent material such as, for example, ferrite, or metal powder such as aluminum or stainless steel, is mixed into hard thermoplastic resin such as polysulfone, denaturated PPO, or polyetherimide, for example.

As shown in FIGS. 6A, 6B and 6C, the first shielding cover 41 and the second shielding cover 42 are arranged such that a projection 43a, for example, provided on a divided face 43 of the first shielding cover 41, which is indicated by slash lines, and a recess 44a, for example, formed in a divided face 44 of the second shielding cover 42. which is indicated by slash lines, are engaged with each other to form the electromagnetic shielding cover 40 which is shown in FIG. 5.

In this manner, the electromagnetic shielding cover is divided by a plurality of members and is arranged whereby mounting and demounting with respect to the connector portion are made easier. Thus, operability is improved. The other function and advantages are similar to those of the aforementioned embodiments.

In connection with the above, even if the electromagnetic shielding cover is not arranged so as to combine two members with each other as described above, but instead to combine three or more members with each other to form the electromagnetic shielding cover, it is possible to obtain similar functions and advantages.

A fourth embodiment of the present invention will be described with reference to FIG. 7.

Figure 7:
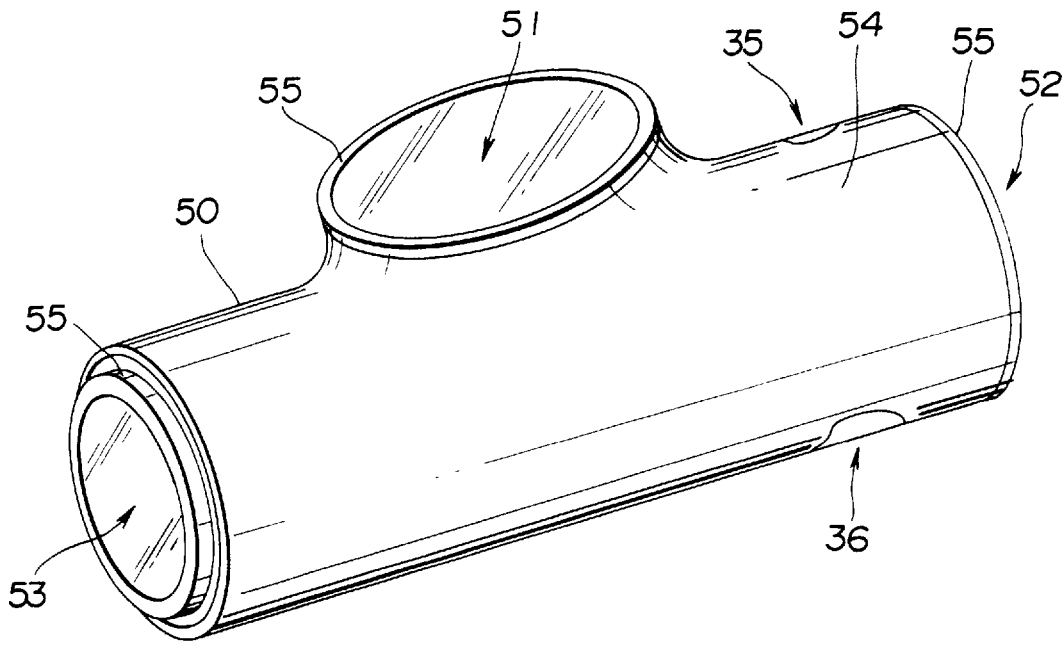
FIG. 7 is a perspective view showing still another arrangement of the electromagnetic shielding cover.

As shown in FIG. 7, an electromagnetic shielding cover 50 in the fourth embodiment is formed which is in the form of a resin sheet such as polyester or polyurethane into which an electromagnetic absorbent material, such as ferrite, or metal powder, such as aluminum or stainless steel, is mixed, or in the form of a sheet in which a metal thin wire, such as stainless steel, is wound.

The electromagnetic shielding cover 50 is formed therein with a connector opening 51 for the electrical cord, an opening 52 on the side of the universal cord and an end-portion opening 53. These openings 51, 52 and 53 are formed such that their respective inner diameter sizes are greater than respective outer diameter sizes of the connector portion 13 and the connector portion 14 for the electrical cord corresponding respectively to the openings 51, 52 and 53. Further, similarly to an inner diameter size of a core or drum 54 of the electromagnetic shielding cover 50, the inner diameter size of the core 54 of the electromagnetic shielding cover 50 is formed to be one size greater than the outer diameter of the corresponding connector portion 13.

In the opening vicinity of the connector opening 51 for the electrical cord, the opening 52 on the side of the universal cord and the end opening 53, a resilient member 55 is arranged which is provided with rubber or a spring which acts to contract or reduce a diameter, with respect to an outer diameter size of the connector portion 13 and the electrical-cord connector portion 14, which are arranged at the respective openings 51, 52 and 53.

With this arrangement, when the connector portion 13, for example, is covered with the electromagnetic shielding cover 50, the inner diameter of each portion of the electromagnetic shielding cover 50 is formed greater than the outer diameter of the connector portion 13. Accordingly, the mounting operation may be smoothly executed. Moreover, after mounting of the electromagnetic shielding cover 50, the elastic member 55 which is arranged in the vicinity of the respective openings is contracted, whereby portions including the connector opening 51 for the electrical cord, the opening 52 on the side of the universal cord and the end opening 53 are tightened.

In this manner, the diameter of the elastic member is reduced to be less than outer diameters of respective members which are arranged on the respective openings in the vicinity of an opening in the electromagnetic shielding cover, and the connector portion is tightened by the elastic member so as to be fixed thereby, whereby the possibility of shift or deviation during operation is eliminated. Thus, it is possible to hold or retain shielding effects during use. Furthermore, the entire electromagnetic shielding cover is formed by shape memory resin including a mixture of electromagnetic absorbent material, such as ferrite, and metal powder, such as aluminum or stainless steel. Thus, after the electromagnetic shielding cover has been mounted on the connector portion, heat is applied to cause deformation of the electromagnetic shielding cover, whereby it is possible to more reliably fix the electromagnetic shielding cover to the connector. The other function and advantages are similar to those of the aforementioned embodiment.

As shown in FIG. 1, the electrical-cord connector 16 to which the electrical cord 15 detachably connected to the video processor 4 is connected is provided on the side of the connector portion 13. Since the electrical-cord connector 16 is provided with the group of contact pins, the electrical-cord connector 16 is efficiently shielded, whereby the shielding ability of the connector portion 13 is considerably improved. Here, radiative-noise reduction countermeasures of the electrical-cord connector 16 of the connector portion 13 will be described.

A fifth embodiment of the present invention will be described with reference to FIG. 8.

Figure 8:
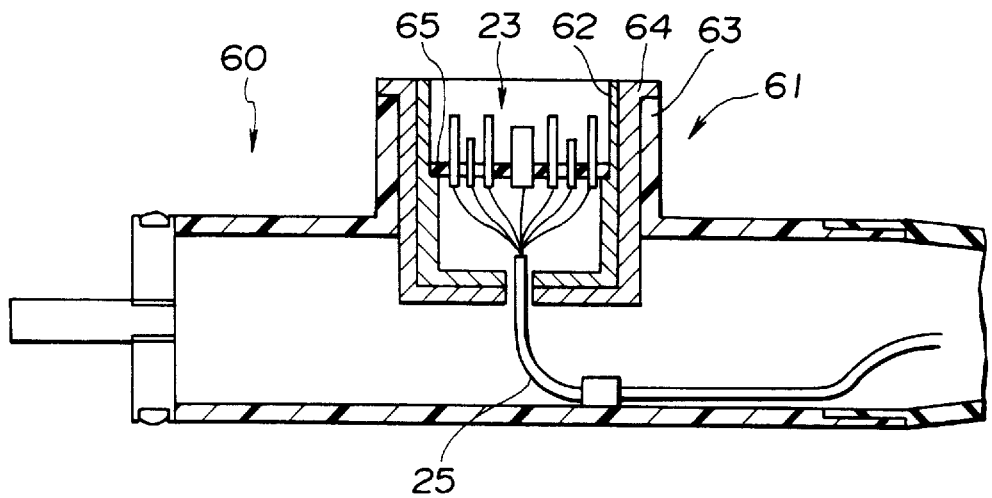
FIG. 8 is a cross-sectional view describing a connector portion in which a radiative-noise reduction member is arranged in an electrical connection portion according to a fifth embodiment the present invention.

As shown in FIG. 8, the electrical-cord connector portion 61 which is provided on the side of a connector portion 60 in the present embodiment comprises an electrical connector body 62, a casing 63 of the connector portion 60, which is formed by synthetic resin such as polysulfone, denaturated PPO, or polyetherimide, and a shielding case 64 arranged between the electrical connector body 62 and the casing 63 and formed by an electromagnetic absorber, a metal conductor, a metal mesh or net wire as a radiative-noise reduction member which wraps the electrical connector body. In this connection, the reference numeral 65 is a substrate for fixing the group of contact pins 23.

In this manner, the shielding case which wraps the outer peripheral portion of the electrical connector body is interposed with respect to the casing, whereby it is possible to efficiently absorb and cut the noises from the electrical connector body which most radiates the noises. Further, since the shielding case is interposed between the casing and the electrical connector body, it is possible to efficiently absorb the radiative noises, irrespectively of the material making up the casing.

A sixth embodiment of the present invention will be described with reference to FIG. 9.

Figure 9:
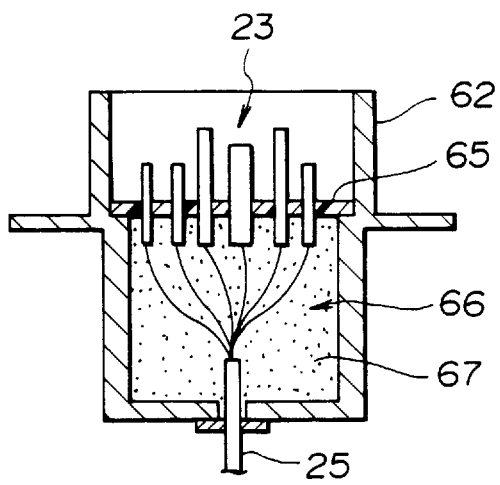
FIG. 9 is a cross-sectional view describing an arrangement in which another radiative-noise reduction member is arranged in an electrical connection portion according to a sixth embodiment of the present invention.

As shown in FIG. 9, in the sixth embodiment, when a space portion 66 which is partitioned by the substrate 65 which fixes the group of contact pins 23 of the electrical connector body 62 is provided with a signal cable 25 or the contact pin 21, the space portion 66 is filled with powder 67 consisting of an electromagnetic absorbent material, such as ferrite. Thus, it is possible to absorb and thereby reduce radiative noises which are generated from the contact pins 23 and the signal cable 25.

Figure 10:
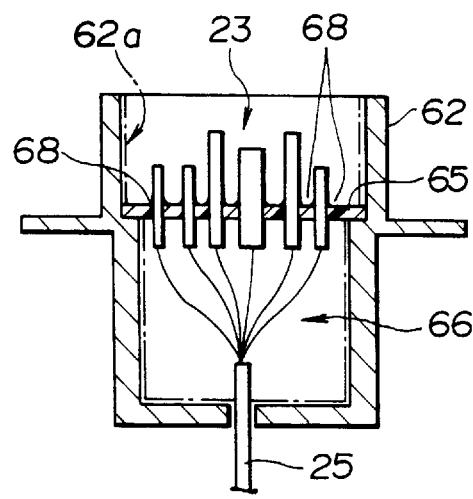
FIG. 10 is a cross-sectional view describing another arrangement of the electrical connection portion in which a radiative-noise reduction member is arranged.

In connection with the above, considering that the substrate 65 is formed by a resin material into which the electromagnetic absorbent material such as ferrite, is mixed, it is possible to further efficiently and effectively absorb and reduce the radiative noises which are generated from the contact pin 23 and the signal cable 25. Moreover, even if the electrical connector 16 which is provided on the electrical cord which is connected to the electrical connector body 62 of the electrical-cord connector portion 61 is filled with the powder 67 consisting of an electromagnetic absorbent material, such as ferrite, it is possible to obtain similar function and advantages. Furthermore, as shown in FIG. 10, the powder electromagnetic absorber 62a, such as ferrite, as indicated by a two-dot-and-chain line in the figure, is coated on the electrical connector body 62 and an inner face of the electrical connector body 62 in the present embodiment, and the group of contact pins 23 is adhesively fixed to the substrate 65. At this time, a powder electromagnetic absorbent material such as ferrite, is mixed with insulation adhesives 68 which are poured in order to fix the group of contact pins 23 and the substrate 65 to one another, whereby it is possible to obtain functions and advantages similar to those of the sixth embodiment.

The following electronic endoscope apparatus will be described. That is, as described above, since there are many connector portions which are made of a resin material, the light source device is arranged as follows, to cover the connector portion, in place of the fact that the connector portion is covered with the electromagnetic shielding cover, whereby it is possible to easily conduct the EMC countermeasures irrespectively of the material and the construction which form the connector portion.

A seventh embodiment of the present invention will be described with reference to FIG. 11.

Figure 11:
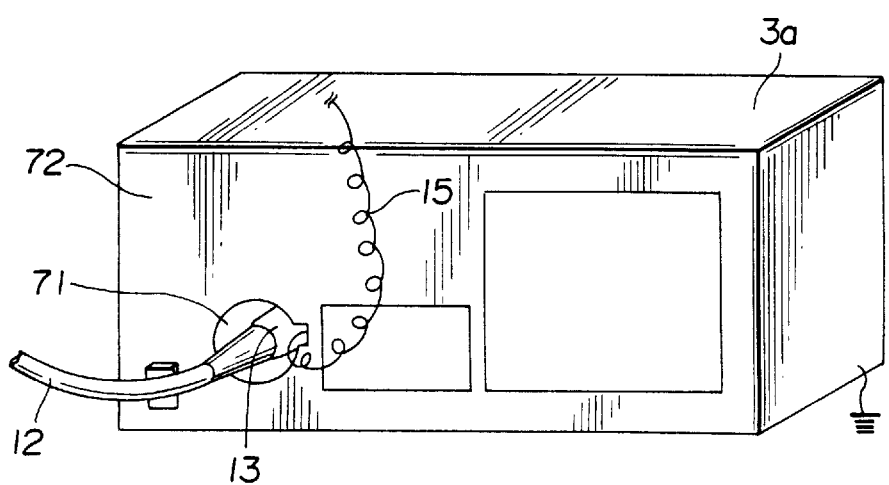
FIG. 11 is a perspective view describing a state in which a connector portion is covered with a metal surrounding or enclosure member that is an electromagnetic interference countermeasure member relating to a seventh embodiment of the present invention.

As shown in FIG. 11, in the seventh embodiment, an outer periphery of the connector portion 13 is surrounded by a metal casing for a light source device 3a instead of covering the connector portion 13 with the electromagnetic shielding cover. Specifically, a receptacle portion 71 with respect to the connector portion 13, which is provided on the light source device 3a, is located at a position which enters into the internal side of the light source device 3a more than a front panel 72. An amount of displacement by which the light source device 3a enters into the internal side from the front panel 72 at this time is set such that, when the connector portion 13 is mounted in the receptacle portion 71, the entire connector portion 13 rests in the internal side of a casing for the light source device 3a. The casing of the light source device 3a is formed by a metal material having conductivity such as, for example, aluminum or iron, and is grounded.

In this manner, the receptacle portion with respect to the connector portion is arranged so as to be provided at the position from the internal side of the light source device more than the front panel of the light source device, whereby, when the connector portion is connected to the light source device, the connector portion enters a state in which it is housed or received into the casing of the light source device. Thus, it is possible to electromagnetically shield the connector portion by the casing made of metal.

Figure 12:
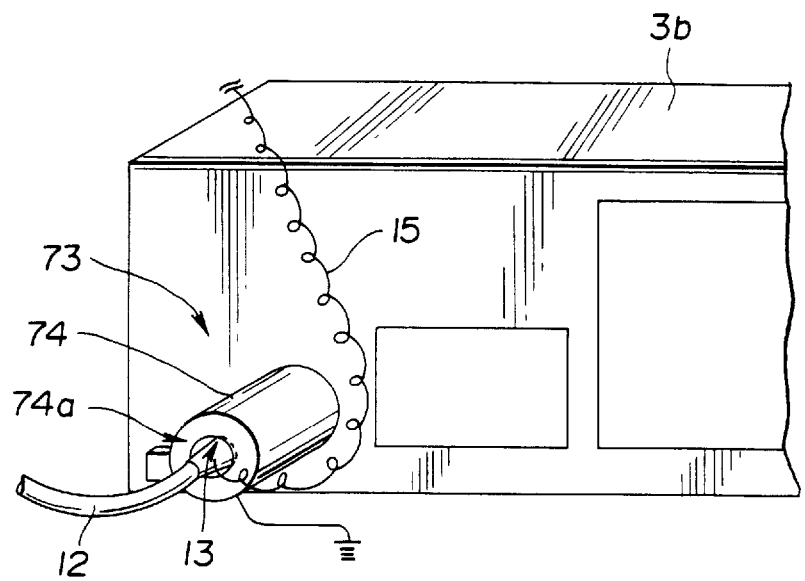
FIG. 12 is a cross-sectional view describing another arrangement of the metal enclosure member.

Further, as shown in FIG. 12, a tubular shielding wall 74 which is formed by a metal material having conductivity, such as, for example, aluminum or iron, may be arranged on a periphery of a receptacle portion 73 of the connector portion 13 which is provided on a light source device 3b. At this time, an inner diameter and a height of the shielding wall 74 is set to a dimension in which, when the connector portion 13 is mounted to the receptacle portion 73, the connector portion 13 is received within the shielding wall 74. Furthermore, the shielding wall 74 is grounded. An opening 74a, on the side of hand, in the shielding wall 74 is made to an opening size which is reduced in diameter to such a degree that the connector portion 13 can pass therethrough.

In this manner, the shielding wall made of the metal, which receives the connector portion mounted to the receptacle portion of the light source device, is arranged such that the connector portion is electromagnetically shielded by the shielding wall. Thus, it is possible to obtain advantages similar to those of the seventh embodiment. Further, since the shielding wall projects from the front panel of the light source device, cleaning or scavenging ability of the surface of the light source device, and ease of maintenance of the light source device are improved.

Figure 13:
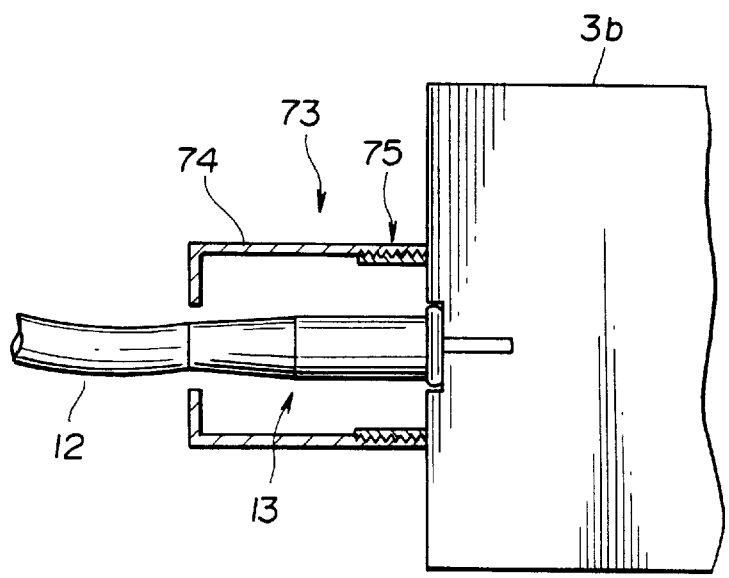
FIG. 13 is a cross-sectional view describing the metal enclosure member which is detachable with respect to a light source device.

In connection with the above, as shown in FIG. 13, a threaded engagement portion 75 is formed on the shielding wall 74 and the light source device 3a so that they are detachable from each other, whereby, when the connector portion 13 and the light source device 3a are detached, the shielding wall 74 is detachable or removable from the light source device 3a. Thus, it is possible to significantly improve ease of detachability between the connector portion 13 and the light source device 3a.

An electromagnetic interference countermeasure member which covers the universal cord 12 having the connector portion 13 at an end thereof will subsequently be described.

An eighth embodiment of the present invention will be described with reference to FIGS. 14 to 16.

Figure 14:
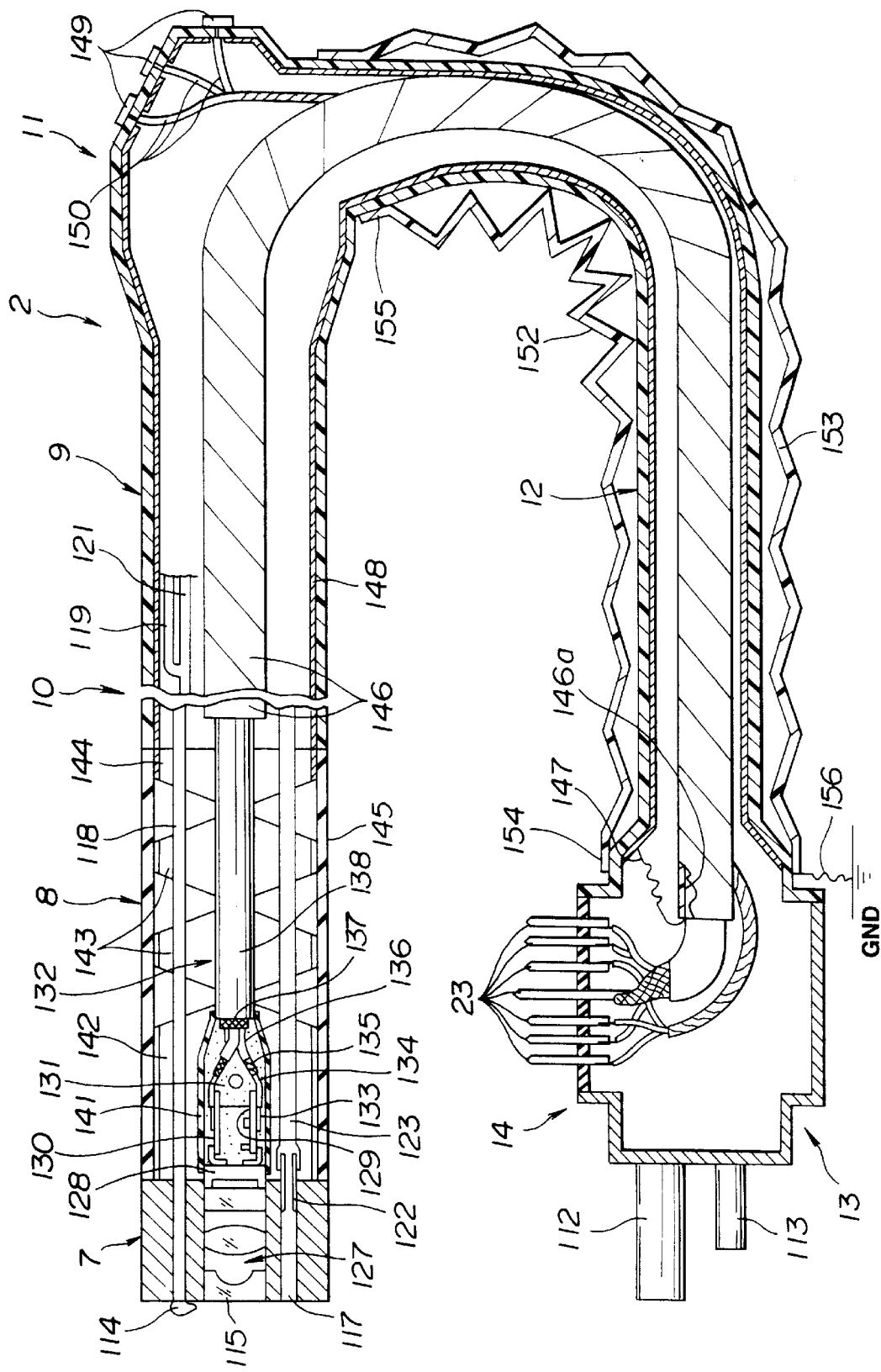
FIGS. 14 to 16 are views describing an eighth embodiment according to the present invention, where

As shown in FIG. 14, the electronic endoscope 2 comprises the elongated insertion portion 10 having elasticity, the operation portion 11 formed at a proximal end of the insertion portion 10, the universal cord 12 which extends from the operation portion 11, and the connector portion 13 which is provided at an end of the universal cord 12.

The connector portion 13 is provided with an electrical connector portion 14 that is provided with the group of contact pins 23, which is connected to the video processor 4, through the electrical cord 15, a light-guide incidence end 112, and a gas supply base 113.

Figure 15:
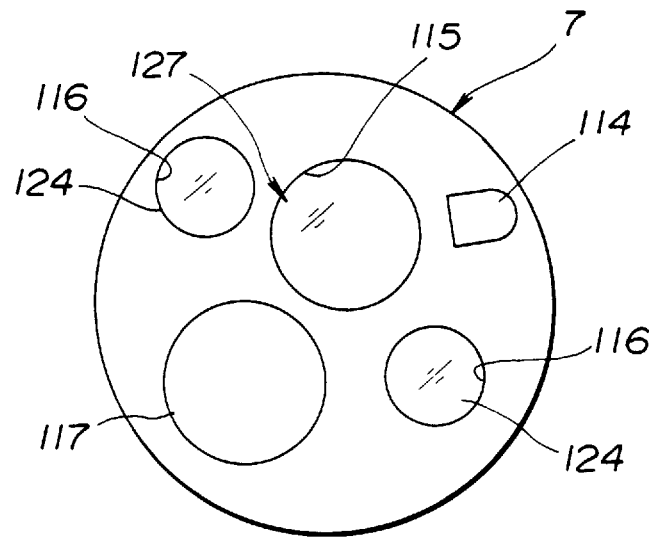

As shown in FIG. 15, the forward-end forming portion 7 is provided, at a forward-end face thereof, with a nozzle 114, an observation window 115 arranged in opposed relation to the nozzle 114, two illumination windows 116 and a forceps outlet 117.

As shown in FIG. 14, the nozzle 114 is connected to a gas-supply.water-supply tube 118 within the curvature portion 8 continuous to the forward-end forming portion 7. The gas-supply. water-supply tube 118 branches into a water supply tube 119 and a gas supply tube 121 within the flexible pipe portion 9. In this state, the gas supply.water-supply tube 118 is inserted and passes through the operation portion 11 and the universal cord 12. At the connector portion 13, the gas supply tube 121 is connected to the gas supply base 113, while the water supply tube 119 is connected to a water supply base (not shown).

Illumination lenses 124 are mounted respectively to the two illumination windows 116 which are formed in the forward-end forming portion 7. Light guide fiber bundles 125 have their respective forward ends which are fixed respectively to the interiors of the illumination lenses 124.

Figure 16:
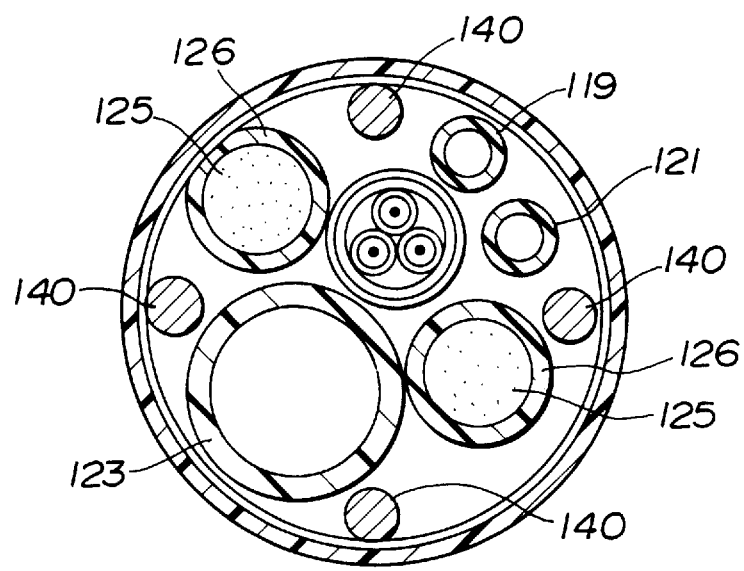

As shown in FIG. 16, the light guide fiber bundles 125 have respective outer peripheral faces thereof which are covered with and protected by light-guide protection tubes 126, respectively. The light guide fiber bundles 125 are inserted and pass through the curvature portion 8, the flexible pipe portion 9, the operation portion 11 and the universal cord 12 under a state covered with these light guide protection tubes 126. The light guide fiber bundles 125 have rearward ends thereof which reach the light-guide incidence end 112 which is provided on the connector portion 13. The light-guide incidence end 112 is connected to the light source device 3, whereby the light guide fiber bundles 125 transmit the illumination light, output the same from the illumination windows 116 and illuminate an object, such as an affected or diseased portion.

The illuminated object focuses into an image at an imaging position by an objective optical system 127 which is mounted to the observation window 115 which is formed between the two illumination windows 116 in the forward-end forming portion 7. At the imaging position, a solid-state image pickup element 128, such as a CCD, is arranged to photoelectrically convert the imaged optical image.

As shown in FIG. 14, the objective optical system 127 is arranged such that the observation window 115 is blocked or closed by a first lens, and the solid-state image pickup element 128 is positioned and fixed to the final lens which forms the objective optical system 127. The solid-state image pickup element 128 is arranged so as to be packaged. A lead is provided in projection on a rear face of an image pickup face. A first circuit substrate 129 and a second circuit substrate 130 are connected to the lead. The first circuit substrate 129 packages a chip condenser or capacitor and two ICs on a ceramic substrate.

One of the ICs is for generating a drive signal which drives the solid-state image pickup element 128, while the other IC is for generating a video signal. The first circuit substrate 129 and the second circuit substrate 130 which extend to the rearward side have their respective rearward ends which are connected to an image pickup cable 132 which is fixed by a cable fixing block 131. Further, a GND of each of the circuit substrates 129 and 130 is conducted to the cable fixing block 131 made of a metal.

A power source for the solid-state image pickup element 128, and the image pickup cable 132 which is formed by a plurality of coaxial lines which execute giving and receiving of the signal and/or a single wire comprise a first metal conductor 133, three coaxial lines including a first insulation resin layer 134, a second metal conductive layer 135 and a second insulation resin layer 136, a third metal conductive layer 137 which surrounds the same and which lumps them together, and a third insulation resin layer 138, for example.

Here, the first insulation resin layer 134, the second insulation resin layer 136 and the third insulation resin layer 138 are arranged such that ferrite particles are mixed into resin, such as Teflon or polyvinyl chloride. The first metal conductor 133 of the image pickup cable 132 is soldered to the first circuit substrate 129 and the second circuit substrate 130. The second metal conductive layer 135 is soldered to the cable fixing block 131.

In connection with the above, the third metal conductive layer 137 is not connected within the forward-end forming portion 7. A rearward end portion of the third metal conductive layer 137 and an end face of the third insulation resin layer 138 are adjusted so as to stay or rest within a first curvature frame or piece 142 which forms the curvature portion 8. The third metal conductive layer 137 is covered with a heat-contraction tube 141 from a position above the solid-state image pickup element 128, the first circuit substrate 129 or the like. The interior of the third metal conductive layer 137 is filled with epoxy resin having insulation Thus, the third metal conductive layer 137 is fixed.

The curvature portion 8 comprises the first curvature piece 142, connection curvature pieces 143, a final curvature piece 144 and a tubular curvature-portion covering rubber 145 which covers them. The first curvature piece 142 is fixed to the forward-end forming portion 7, while the final curvature piece 144 is fixed to the flexible pipe portion 9. The second insulation resin layer 136 and the connection curvature pieces 143, the connection curvature pieces 143 and the final curvature piece 144, and the connection curvature pieces 143 and the connection curvature pieces 143 are connected to each other to provide angular movement.

A curvature mechanism is formed in which an angle knob (not shown), which is provided on the operation portion 11, is operated whereby angle wires, which are connected to the angle knob, are pushed and pulled so as to be capable of curving the curvature portion 8 in various directions, including an upper direction, a lower direction, a left-hand direction and a right-hand direction. As shown in FIG. 16, angle wires 140 are arranged within the insertion portion 10 respectively along four directions, and have forward ends thereof which are fixed to the first curvature piece 142.

The image pickup cable 132 is arranged such that, within the flexible pipe portion 9, the operation portion 11, the universal cord 12 and the connector portion 13, shielding tapes 146 in which a conductive paint 146*a* is applied to one face of a strip- or strap-like member which is wide in width, which is formed by an insulation resin material is wound further from the upper portion of the third insulation resin layer 138. At this time, a conductive face is formed on the side of the third insulation resin layer 138, and the opposite external face is insulated. A jumper wire 147 is so drawn out as to be conducted to the conductive paint 146*a*, from the end face within the connector portion 13 so that the shielding tapes 146 are connected to a metal blade 148 on an inner face of the universal cord 12.

The metal blade 148 is provided on portions of the flexible pipe portion 9, the operation portion 11, the universal cord 12 and the connector portion 13, and they are all connected to each other. The third insulation resin layer 138 is arranged such that, within the connector portion 13, the image pickup cable 132 is strip-molded similarly to the inside of the curvature portion 8, and the first metal conductor 133, the second metal conductive layer 135 and the third metal conductive layer 137 are connected to the group of contact pins 23.

Moreover, the operation portion 11 is provided with a plurality of operation switches 149 which execute a freeze indication. Each of the operation switches 149 is connected to an associated switch cable 150. These switch cables 150 are inserted and pass through the interior of the universal cord 12 in a twisted intertwined state, for example. Within the connector portion 13, each of the switch cables 150 is soldered to the associated one of the contact pins similarly to the image pickup cable 132.

The group of contact pins 23 are connected to the video processor 4 through the electrical cord 15. In the present embodiment, the universal cord 12 is covered with a universal cord cover 152.

The universal cord cover 152 is constructed of extendible and retractable bellows-like insulation resin. An inner face thereof is provided with a metal evaporation layer 153 which serves as an electromagnetic interference countermeasure member.

A fixing portion 154 on the side of the connector is provided on the side of the connector portion 13 of the universal cord cover 152, and a fixing portion 155 on the side of the operation portion is provided on the side of the operation portion 11. The fixing portion 154 on the side of the connector and the fixing portion 155 on the side of the operation portion are made of rubber or a spring which has a smaller diameter similarly to the elastic member 55 which is arranged in the vicinity of the opening illustrated in FIG. 7. The fixing portion 154 and the fixing portion 155 are arranged so as to be firmly fixed to the connector portion 13 and the operation portion 11, respectively.

Furthermore, an earth line 156 comes out from the metal evaporation layer 153 of the fixing portion 154 on the side of the connector. Thus, the arrangement is such that the earth line 156 can be conducted to GND, which is provided separately.

Furthermore, as shown in FIG. 16, the image pickup cable 132 is arranged substantially at a center within the flexible pipe portion 9. A forceps insertion and passage tube 123, the light-guide protection tubes 126, the water supply tube 119 and the gas supply tube 121, which are formed by the electromagnetic absorbent material, are arranged around the image pickup cable 132.

In this manner, the universal cord cover having the shielding member is provided on the universal cord, whereby it is possible to reduce radiation of the radiative noises from the image pickup cable and the switch cables, and mixture of the noises to the image pickup cable and the switch cables. Furthermore, since the universal cord cover is formed in the form of a bellows, there is less chance that the elasticity of the universal cord is affected. Further, since the universal cord cover is detachable with respect to the universal cord, sufficient shielding effects can be expected also with respect to an arrangement in which the shielding countermeasures are not applied to the electronic endoscope body. Since the earth line is provided on the universal cord cover per se, it can also deal with any endoscope system.

Moreover, since it is detachable, if the universal cord cover is mounted to the universal cord when it is used in combination with a plurality of pieces of equipment, particularly pieces of equipment susceptible to the influence of the noises or pieces of equipment likely to generate the noises, it is possible to simply or easily perform effective EMC countermeasures. At other times, if the electronic endoscope is used without the universal cord cover being mounted, it is possible to use the same as an ordinary universal cord. That is, it is possible to be used as an electronic endoscope having the universal cord which is superior in operability, having sufficient elasticity.

Moreover, if the universal cord cover is used as a disposable one, it is preferable also from health or sanitation point of view.

Furthermore, the arrangement is such that a portion of the image pickup cable from the insertion portion to the connector portion is covered with the shielding tape which functions as the electromagnetic interference or disturbance countermeasure member, and this is maintained to the same electrical potential as that of the metal blade which serves as the shielding metal for the electronic endoscope. Accordingly, the shielding advantages further increase. On one hand, since the shielding tape is not provided on the curvature portion, a fill rate or ratio within the curvature portion does not rise, and there is no interference with the curvature operation. In this connection, even if the fill ratio rises more or less within the flexible pipe portion and the universal cord, since tight turning is not required as the curvature portion, there is no problem. Since conduction is made within the connector portion with respect to the shielding metal, operability is improved.

Furthermore, the arrangement allows the image pickup cable to be arranged substantially at the center within the flexible pipe portion, and the visceral objects, including the electromagnetic absorbent material, are arranged around the image pickup cable. Accordingly, the image pickup cable is surrounded by the shielding member. Thus, the shielding advantages are increased. In this connection, since the electromagnetic absorbent material such as ferrite, is included within each of the insulation resins of the image pickup cable, the shielding advantage is increased.

A ninth embodiment of the present invention will be described with reference to FIGS. 17 and 18.

Figure 17:
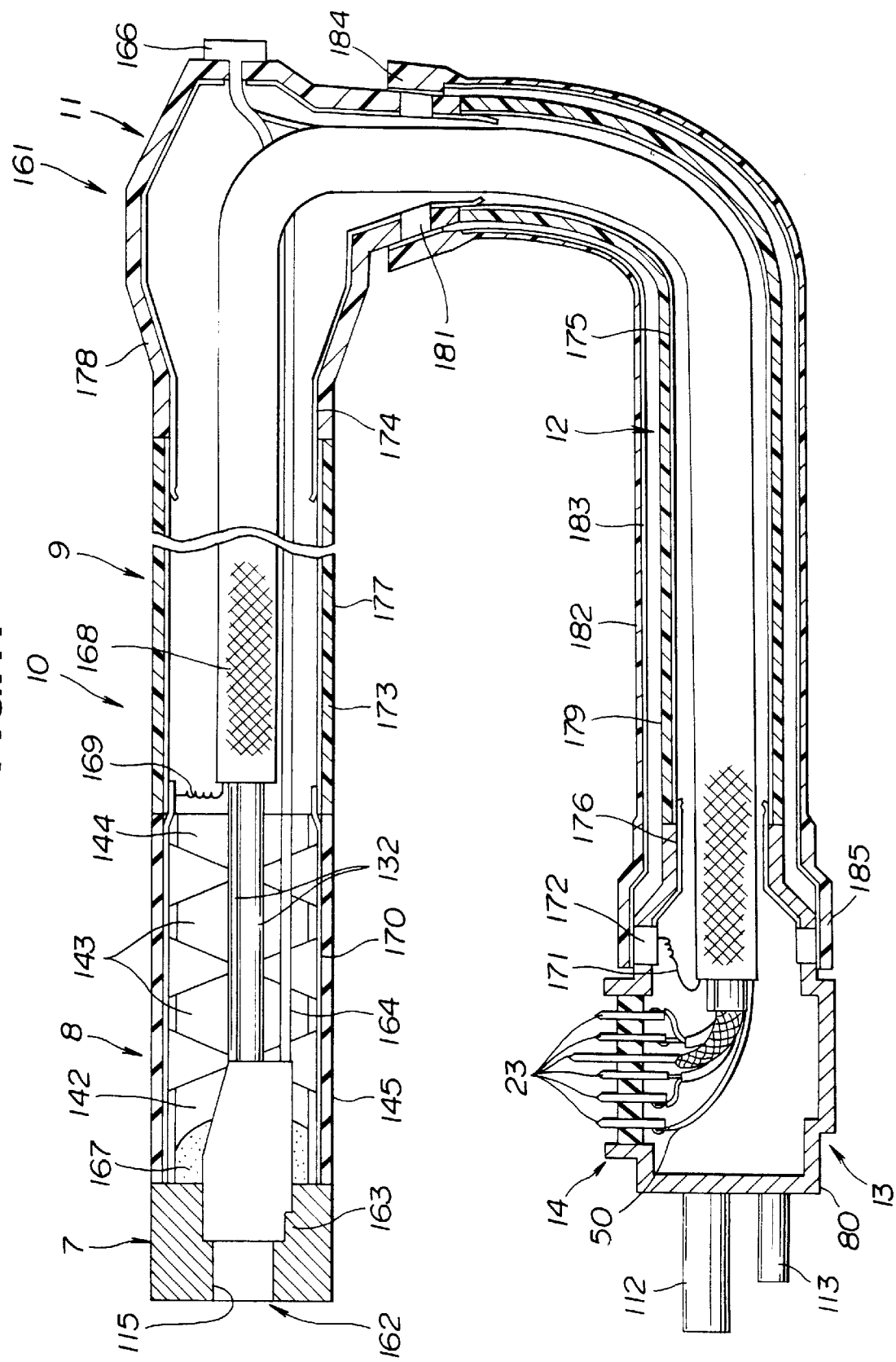
FIGS. 17 and 18 are views describing a ninth embodiment according to the present invention, where

As shown in FIG. 17, an enlargement objective optical system 162, for example, is provided on the observation window 115 of the forward-end forming portion 7. The enlargement objective optical system 162 is an objective optical system which has a movable lens so that enlarged observation is possible. The enlargement objective optical system 162 is image-formed to a solid-state image pickup element (not shown) within an image pickup 163. The image pickup 163 is arranged as a unit which includes the solid-state image pickup element 128, the first circuit substrate 129, etc.

The movable lens which forms the enlargement objective optical system 162 is movable by means of a focus wire 165 within a focus-wire protection pipe 164 which is pushed and pulled. The focus wire 165 is operated by a focus switch 166 which is provided on the operation portion 11. The focus switch 166 is connected to the contact pins within the connector portion 13 through the switch cables 150 which are inserted into and which pass through the universal cord 12.

The image pickup 163 is fixed to the forward-end forming portion 7. However, the circumstances thereof are filled with a solid lubricant 167 containing the ferrite particles. Further, the two image pickup cables 132 and 132 are connected to the image pickup 163.

Figure 18:
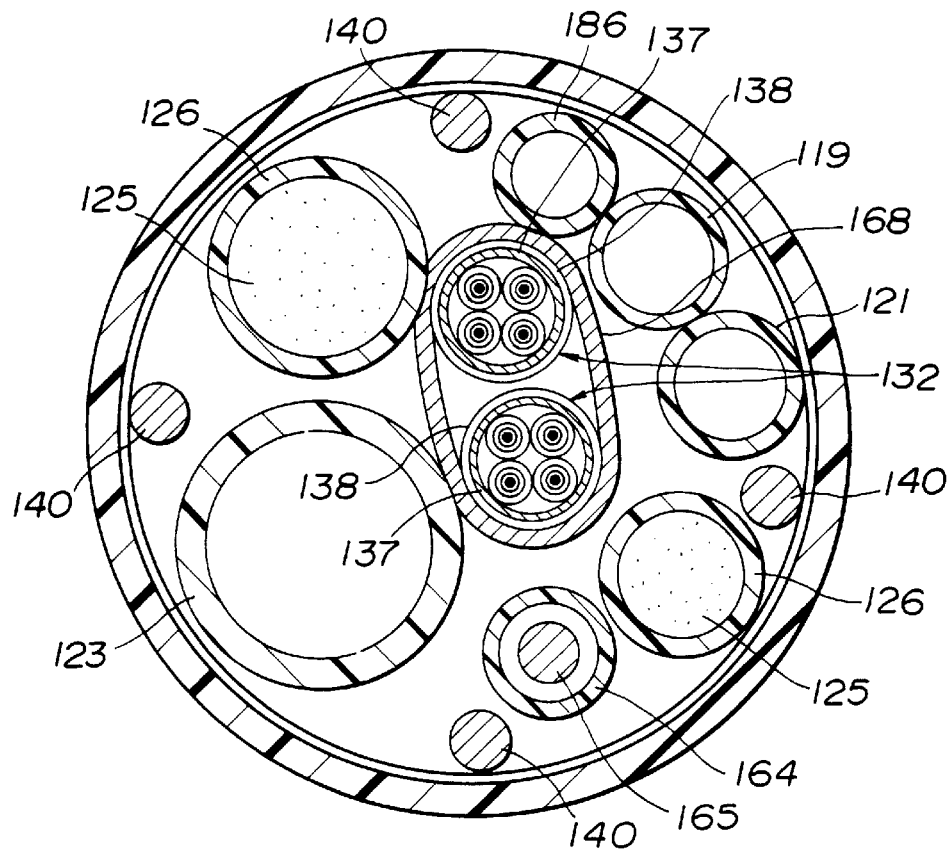

As shown in FIG. 18, the image pickup cable 132 comprises four coaxial cables, the third metal conductive layer 137 which covers the outside thereof, and the third insulation resin layer 138. However, the image pickup cable may comprise, not only the coaxial cable, but also a combination of single wires each of which comprises a conductor and an insulation coating.

The image pickup cables 132 are arranged such that, within the flexible pipe portion 9, the operation portion 11 and the universal cord 12, these two image pickup cables 132 are put together, and the put-together cables are covered with an electromagnetic disturbance or countermeasure cover 168 that is a magnetic interference countermeasure member, from the outside thereof. The image pickup cables 132 are connected to the contact pins which are provided on the electrical contact portion 11, within the connector portion 13.

The electromagnetic interference countermeasure cover 168 is arranged such that metal thin wires are knitted, with a cross-angle of 90°. The electromagnetic interference countermeasure cover 168 is arranged such that a forward-end jumper wire 169 is drawn out from an end of the electromagnetic interference countermeasure cover 168 on the side of the curvature portion 8, that is, a forward end of the electromagnetic interference countermeasure cover 168 and is connected to the end, on the side of the flexible pipe portion or elastic tube 9, of a curvature-portion metal blade 170 which covers the curvature pieces 142, 143 and 144 of the curvature portion 8. Further, a rearward-end jumper line 171 is drawn out from the end of the electromagnetic interference countermeasure cover 168, and is connected to an inner face of a metallic universal-cord-cover conduction portion 172.

The curvature-portion metal blade 170, a flexible-pipe-portion metal blade 173, an operation-portion metal portion 174, a universal-cord metal blade 175 and a connector-portion metal portion 176 are connected at respective end portions thereof to each other, and are conductive with each other.

The curvature-portion metal blade 170 has an outer peripheral face thereof which is covered with curvature rubber 145. The flexible-pipe-portion metal blade 173 is covered with an elastic pipe resin tube 177 which acts as an armor member for the flexible pipe portion 9. The operation-portion metal portion 174 is covered with an operation-portion armor member 178 which is formed by resin. The universal-cord metal blade 175 is covered with an electrical universal-cord resin tube 179 which serves as an shield member for the universal cord 12. The universal-cord resin tube 179 has a rearward end thereof which is fixed to a metallic shield member 80 of the connector portion 13.

A universal-cord-cover conductive portion 181 which draws out the operation-portion metal portion 174 on the inner face of the operation portion 11, to the outer face of the operation portion 11 is provided adjacent to the operation-portion metal portion 174 on the side of the universal cord 12. Similarly, the universal-cord-cover conduction portion 172 which draws the connector-portion metal portion 176 on the inner face of the connector portion 13, out to the outer face of the connector portion 13, and which is conducted to a conductive member of a universal cord cover 182 is provided adjacent to the electrical contact portion 11 of the connector-portion metal portion 176.

The universal cord cover 182 which covers the universal cord 12 is made of elastic insulation resin. A universal-cord-cover metal blade 183 is laminated upon the inner face of the universal cord cover 182. The universal cord cover 182 has both end portions thereof at which a fixing portion 84 on the side of the operation portion and a fixing portion 85 on the side of the connector are provided respectively, and which are so arranged as to be detachable with respect to the operation portion 11 and the connector portion 13.

Upon mounting of the universal cord cover 182, the universal-cord-cover metal blade 83 is respectively in contact with the universal-cord-cover conduction portion 172 and the universal-cord-cover conductive portion 181 and is conducted thereto. In connection with the above, as shown in FIG. 18, a forward water-supply tube 186 is provided within the insertion portion 10.

With the above-described arrangement, it is possible to make the curvature-portion metal blade 170, the flexible-pipe-portion metal blade 173, the operation-portion metal portion 174, the universal-cord metal blade 175 and the connector-portion metal portion 176, the electromagnetic interference countermeasure cover 168, and the universal cord-cover metal blade 183 of the universal cord cover 182, to the same potential.

Further, as shown in FIG. 18, the image pickup cables 132 are arranged substantially at a center within the flexible pipe portion 9, and the forceps insertion and passage tube 123, the light-guide protection tubes 126, the water supply tube 119, the gas supply tube 121, the forward water-supply tube 186, and the focusing-wire protection pipe 164, which are made of the electromagnetic absorbent material, are arranged so as to surround the same. The forward water-supply tube 186 is a pipe line for supplying water forwardly, which is used often in an endoscope for a lower-portion digestive organ.

In this manner, since a portion which is conducted to the shield metal is provided at a portion at which the universal cord cover is mounted, it is possible to be made simply to the potential the same as those of the universal cord cover and the shield metal. This results in improved shielding. Moreover, although there is the likelihood of a floating potential state, if the jumper line is drawn out from the end portion of the universal cord cover, it is possible to simply be connected to GND.

Furthermore, also even at the time when the universal cord cover is not mounted, it is possible to simply connect the shield metal to GND by a metal portion of the mounting portion.

Moreover, since the image pickup cable is covered with the electromagnetic interference countermeasure cover with two collected together, handling of the image pickup cable is made easier. Further, since the electromagnetic interference countermeasure cover is conducted at two locations before and behind the same, a conductive state is further stabilized, and, even in a case where one of them is unfastened, it is possible to maintain the shielding function. In this connection, by the fact that, if the visceral objects within the insertion portion increase, it is only to use the tube into which the electromagnetic absorbent material is mixed, it is possible to obtain the shielding advantages without being undesirably large in diameter.

In connection with the above, the present invention has a detachable arrangement in which the universal cord cover 152 in the eighth embodiment can be mounted to and can be demounted from the universal cord 12 from the side of the connector portion 13 or the side of the insertion portion 10. However, the detachable arrangement includes, for example, also an arrangement in which the universal cord cover 152 is fixed in the vicinity of the connector portion 13 such that the bellows is folded up, and, in a case where the universal cord 12 is required to be covered, the bellows extends, and the extended end portion, that is, the fixing portion 155 on the side of the operation portion is fixed in the vicinity of the operation portion 11.

Furthermore, whenever the universal cord cover 152 is fixed in such a manner that the bellows is folded up in the vicinity of the connector portion 13, it is possible to use it as a normal electronic endoscope.

The arrangement may be such that means for simply releasably folding up the universal cord cover 152 to, for example, the connector portion 13 to fix or receive the same is provided so that the universal cord cover 152 is held under a fixed state in accordance with the use environment, the fixing is released, and the bellows extends as described above, in order to fix the fixing portion 155 on the side of the operation portion, in the vicinity of the operation portion 11.

In connection with the above, the present invention is not limited to the electronic endoscope in which the image pickup means is installed in the forward end portion of the insertion portion and which has the universal cord which is inserted and passes through the image pickup cable connected to the image pickup means. The present invention is applicable also to a case of a TV-camera equipped endoscope in which a TV camera which has built therein image pickup means such as a solid-state image pickup element is equipped in an ocular portion of an optical endoscope which has an image guide.

Specifically, the present invention is applicable also to an arrangement in which a cord which is generally called a "camera cord" having one end thereof extending from a TV camera and the other end at which a connector connected to a video processor or a camera control unit is provided and through which an image pickup cable connected to image pickup means within the TV camera is inserted and passes can detachably be covered by a cord cover which has electromagnetic interference countermeasure function.

A tenth embodiment of the present invention will be described with reference to FIGS. 19 to 24.

Figure 19:
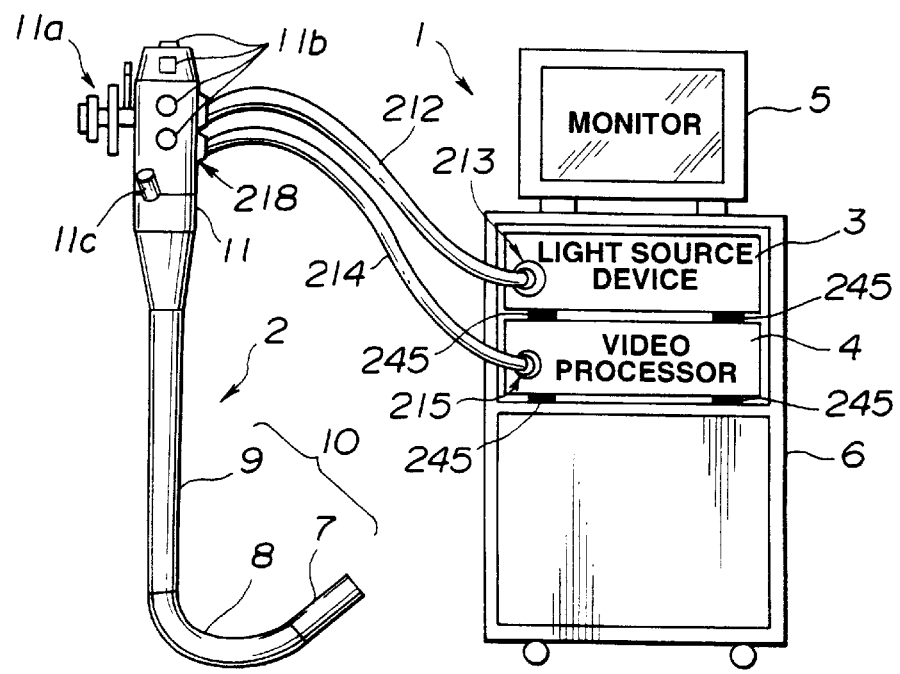
FIGS. 19 to 24 are views describing a tenth embodiment according to the present invention, where

As shown in FIG. 19, the electronic endoscope 2 according to the tenth embodiment is arranged such that a universal cord 212 and a signal cable 214 extend therefrom, the universal cord 212 having a gas supply tube, a water supply tube, a light guide for transmitting an illumination light from an end of the operation portion 11, and various kinds of signal lines being inserted and passing through the signal cable 214. A connector 213 for the light source which is detachable to the light source device 3 is provided at an end of the universal cord 212. A metallic electrical connector 215 having a structure which can detachably be mounted to the video processor 4 is provided on an end of the signal cable 214.

Figure 20:
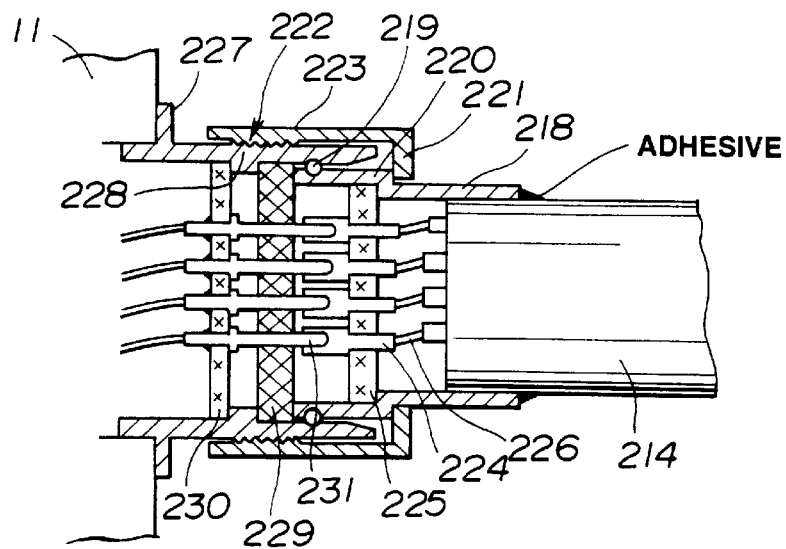

In connection with the above, the side of the operation portion 11 that is the proximal end of the signal cable 214 is formed as shown in FIG. 20. That is, as shown in FIG. 20, a base 218 made of a metallic material is integrally adhesively fixed to the end of the signal cable 214. An O-ring 219 is provided around an outer periphery of the base 218. Furthermore, an abutment 221 which is abutted against a step 220 which is formed on the base 218 and a connection member 223 having, on an inner peripheral face thereof, a threaded portion 222 are inserted outwardly on the outer periphery of the base 218. Moreover, a plurality of electrical contacts 224 are fixed to the inner peripheral side of the base 218, through a fixing plate 225. A core wire 226 within the signal cable 214 is fixed to the associated one end of each of the electrical contacts 224 by solder or adhesives having electrical conductivity. In connection with this, in the present figure, the core wire 226 is illustrated as being a single line, but may be a coaxial line.

On one hand, the operation portion 11 is provided with a signal-cable receipt base 227. The signal-cable receipt base 227 has an outer periphery thereof at which a threaded portion 228 is provided which is threadedly engaged with the threaded portion 222. The signal-cable receipt base 227 is provided on the inner periphery thereof with contact pins 231 which are engageable respectively with the electrical contacts 224 through a fixing plate 229 and a fixing plate 230.

Figure 21:
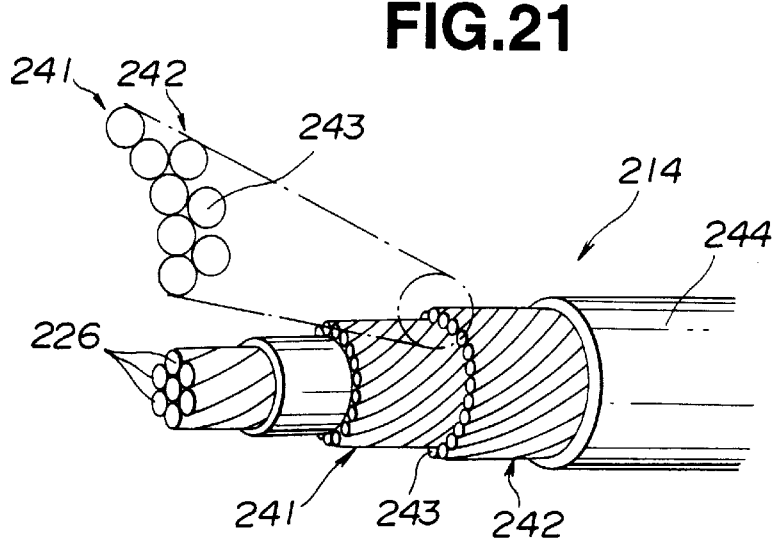

As shown in FIG. 21, in the signal cable 214, each of a first shielding layer 241 and a second shielding layer 242 is provided at an outer periphery of a bundle which is formed in such a manner that the core wire 226 is twisted. The first shielding layer 241 and second shielding layer 242 are arranged such that metal thin conductors or lead wires 243 such as, for example, a copper wire, a copper alloy wire and a stainless steel wire are spirally wound in the same direction. In this manner, the first shielding layer 241 and the second shielding layer 242 are so arranged as to be wound in the same direction whereby the conductors 243 which are double piled up to each other without a gap, as shown in an enlarged view in FIG. 21. Thus, this arrangement ensures that the noises which leak from the gap between the first shielding layer 241 and the second shielding layer 242 are reduced. At this time, of the plurality of core wires 226, a signal line having a high drive frequency, that is, a signal line which is easy to emanate the noises, for example, a horizontal-drive-pulse line is twisted or bundled in such a way that the pulse line becomes a center of the bundle, whereby the signal line is shielded by another core wire 226, so that the arrangement is such that it is difficult for noises to be radiated.

Furthermore, the signal cable 214 is covered with an insulation jacket 244 which is made of 4–6 fluoride resin, or 4-fluoride ethylene perfluoro alkoxy ethylene copolymer resin.

Moreover, one end of the first shielding layer 241 and the second shielding layer 242 are connected to a video ground of the video processor 4 and the other end thereof may be connected to a video ground of the CCD 10 at the forward end of the electronic endoscope 2, through the electrical contacts 224 and the contact pins 231.

Furthermore, in order to reduce the radiated noises from the peripheral devices, such as the light source device 3, the video processor 4, etc., as shown in FIG. 19, the casing of the light source device 3, the casing of the video processor 4 and the cart 6 are conducted to each other through conductive materials 245 which are provided on the casing of the light source device 3 and the casing of the video processor 4 and are grounded.

Figure 22:
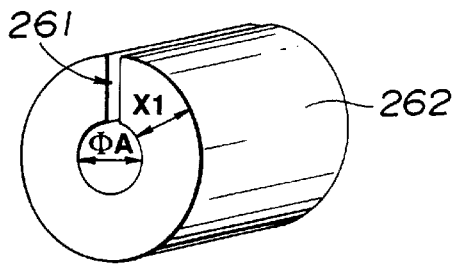
Figure 23:
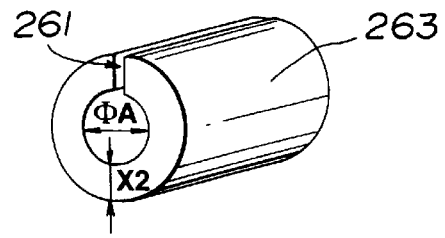
Figure 24:
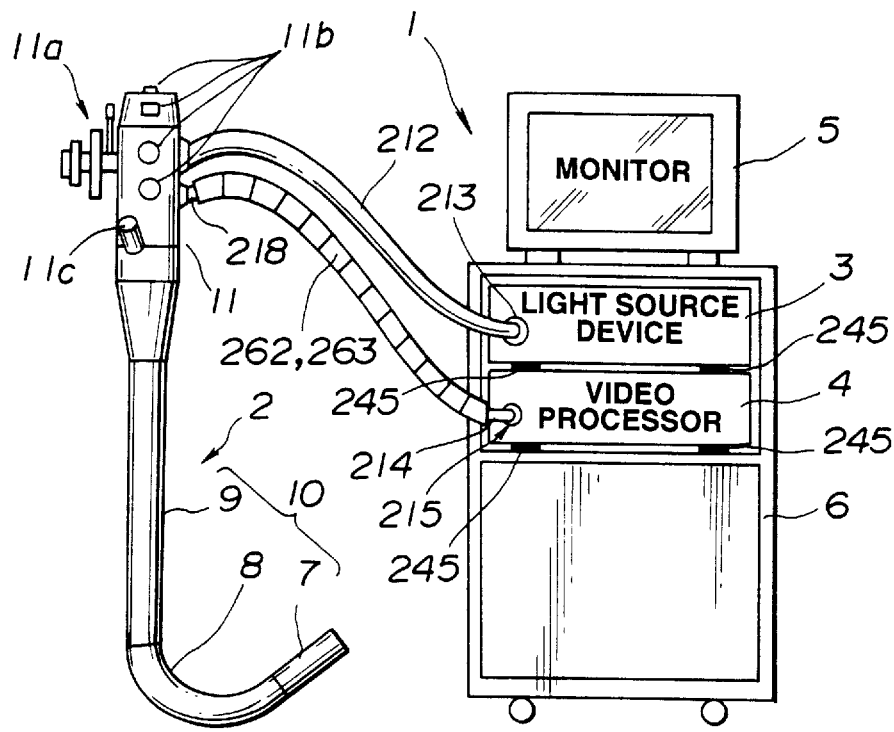

Furthermore, the arrangement is as follows. That is, in order to change or alter efficiency which reduces the radiative noises in accordance with the external environments at a location where the endoscope apparatus 1 is used, at least two kinds of electromagnetic absorbent members which differ only in wall thickness, including a first electromagnetic absorbent member 262 made of an electromagnetic absorbent material such as ferrite, for example, provided with a cut-out 261 whose inner diameter as shown in FIG. 22 is substantially equal to an outer diameter φA of the signal cable 214 and whose wall thickness is x1, a second electromagnetic absorbent member 263 made of an electromagnetic absorbent material which has the cut-out 261, which differs only in wall thickness from the first electromagnetic absorbent member 262, which is substantially equal to the outer diameter φA of the signal cable 214 shown, for example, in FIG. 23, whose wall thickness is x2 are prepared, and the like, whereby the electromagnetic absorbent member whose wall thickness is adequate is selected by the external environment, and, as shown in FIG. 24, the electromagnetic absorbent member is arranged at the signal cable 214 through the cut-out 261 and is used.

In this manner, the signal cable is provided exclusively for signal transmission. Whereby it is possible to sufficiently conduct the EMC countermeasures to the signal cable. Further, since it is arranged detachably to the signal cable through the base which is separate from the electronic endoscope and which is made of a metal, specific or special EMC countermeasures are unnecessary to be conducted to the electronic endoscope and the universal cord. Thus, it is made possible to realize an easily-assembled electronic endoscope apparatus having low cost.

Furthermore, the electromagnetic absorbent member is suitably arranged at the signal cable in accordance with the external environments whereby it is possible to reduce radiation of the unnecessary radiative noises from the signal cable and mixture of the unnecessary radiative noises to the signal cable.

Further, the signal cable is arranged such that the base is inserted into the signal-cable receipt base, and is threadedly engaged therewith, whereby the electrical contact and the contact pins are connected to each other to provide electrical conduction between them. Thus, it is possible to watertightly and detachably fix the signal cable to the operation portion by the O-ring.

An eleventh embodiment of the present invention will be described with reference to FIGS. 25 and 26.

Figure 25:
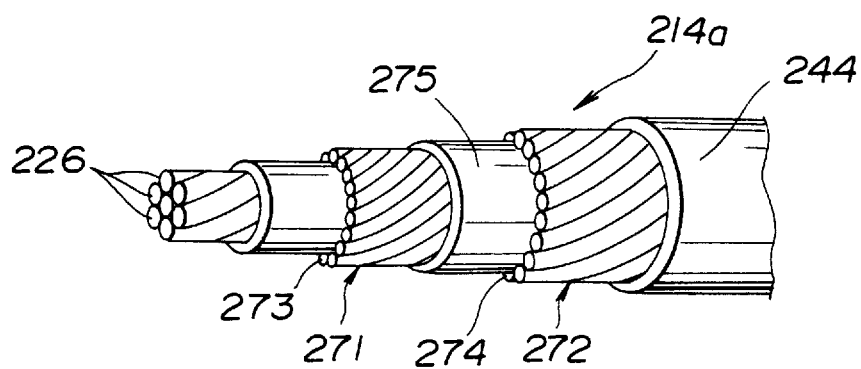
FIGS. 25 and 26 are views describing an eleventh embodiment according to the present invention, where
Figure 26:
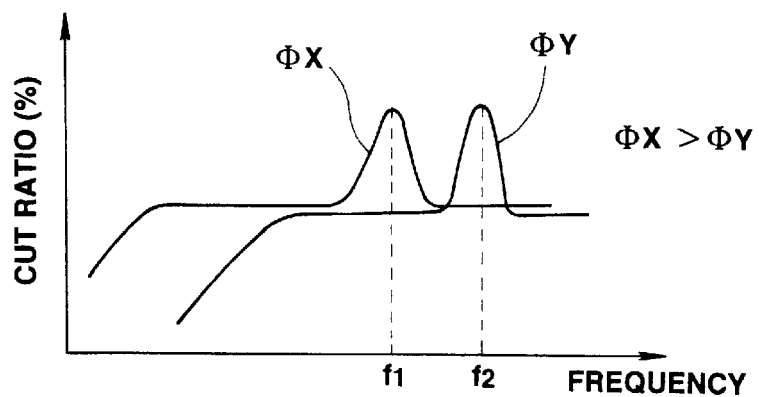

As shown in FIG. 25, a signal cable 214a in the eleventh embodiment is set such that a diameter of the lead wire 73 of the double-layer first shielding layer 71 having the metal conductivity, which is wound in the same direction, and a diameter of the lead wire 73 of the second shielding layer 72 are set different from each other. Moreover, the insulation layer 75 made of synthetic resin, such as 4-fluoride ethylene resin, is provided between the first shielding layer 71 and the second shielding layer 72. The other arrangement is similar to that of the tenth embodiment.

Generally, there is a relationship between the diameter of the conductor or the lead wire and the frequency of the noises which can be attenuated such that it is possible to exclude a certain frequency band according to the diameter of the element wire. Moreover, as shown in FIG. 26, when the diameter of the lead wire is φX and φXY, for example, frequencies f1 and f2 which can efficiently be attenuated are different from each other.

In the eleventh embodiment, the insulation layer is interposed between the first shielding layer and the second shielding layer which cooperate with each other to form the signal cable, and the first shielding layer and the insulation layer are independent of each other. Thus, a difference in diameter between the lead wire of the first shielding layer and the lead wire of the second shielding layer clearly appears. Accordingly, in addition to the advantages of the tenth embodiment, the characteristics shown in FIG. 26 are utilized, and a wider frequency region is attenuated by one of the two lead wires which have diameters thereof different from each other, and a frequency of noises due to an electrocautery, for example, 300–600 kHz, is the most well attenuated by the other lead wire. Thus, it is possible to excuse the noise countermeasure more efficiently.

Lastly, an electromagnetic interference countermeasure member which covers an external device to which the connector portion is connected, according to a twelfth embodiment of the present invention will be described with reference to FIG. 27.

Figure 27:
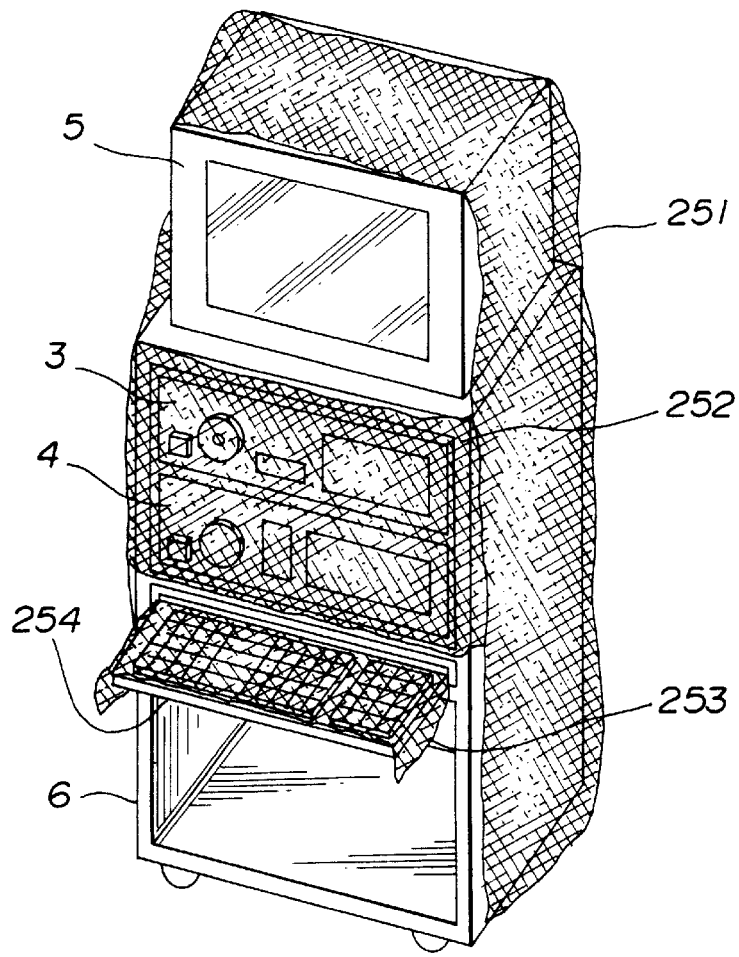
FIG. 27 is a perspective view of a twelfth embodiment of the present invention including an external device and a cart on which the external device is mounted are covered with a shielding curtain that is an electromagnetic interference countermeasure member.

As shown in FIG. 27, in the twelfth embodiment, as the EMC countermeasures for the pieces of peripheral equipment of the electronic endoscope apparatus 1 in FIG. 1 or 19, which is provided with the electronic endoscope, the cart 6 and the periphery of the monitor 5 are covered with a first shielding curtain 251 which is so formed, for example, as to be wound by stainless metal element wires, on one hand, front faces of the light source device 3 and the video processor 4 are covered with a second shielding curtain 252 which is wound similarly to a first shielding curtain 351. An upper face of a keyboard 254 which inputs the indication with respect to the video processor 4 is covered with a keyboard cover which is made of an electromagnetic absorbent material such as, for example, ferrite, or is covered with a third shielding curtain 253 which is wound similarly to the first shielding curtain 251.

In this manner, because the external device which forms the electronic endoscope apparatus is covered with the shielding curtain, it is possible to reduce radiation of the undesirable radiative noises and a mixture of the undesirable radiative noises. Thus, because the shielding curtain is always available as a member which forms the electronic endoscope apparatus, when it is used in combination with a piece of equipment which is likely to be affected by the noises, or a piece of equipment which is likely to generate the noises, if the shielding curtain is covered on the external device which is formed as a system as occasion demands, it is possible to easily conduct the effective EMC countermeasures. At other times, the external device is used without the shielding curtain being mounted thereon.

In the present invention, it is apparent that working modes or embodiments different in a wide range can be formed on the basis of the present invention without departing from the spirit and scope of the present invention. The present invention is not restricted by any specific embodiment being limited by the appended claims.

What is claimed is:

1. An electronic endoscope apparatus comprising:

an electronic endoscope having an insertion portion including a solid-state image pickup element; and a plurality of external devices including at least a light source device for supplying an illumination light to the electronic endoscope and a video processor for processing an electrical signal which is transmitted from the solid-state image pickup element of said electronic endoscope to produce a video signal, wherein an electrical connection portion for electrically connecting said electronic endoscope and said video processor is provided on a connector portion which is provided at one end of one of a universal cord and a signal cable, one of which contains a signal line connecting said electronic endoscope and said video processor, wherein said electronic endoscope apparatus is provided with an electromagnetic interference countermeasure member which covers at least one of said connector portion, said universal cord, said signal line and said external devices, wherein said signal line transmits an electrical signal which is photoelectrically changed by the image pickup element provided at a forward end of said endoscope insertion portion, and lead wires having different diameters are spirally wound around said signal line, and wherein one end of said lead wires is connected to a video ground of said video processor and another end of said lead wires is connected to a video ground of said image pick-up element.

2. An electronic endoscope apparatus according to claim 1, wherein said electromagnetic interference countermeasure member further comprises a metallic member surrounding an outer periphery of said connector portion, and wherein said metallic member is grounded.

3. An electronic endoscope apparatus according to claim 2, wherein said metallic member comprises one of said light source device and said video processor, wherein said electronic endoscope apparatus further comprises a detachable portion which is detachable with respect to said connector portion and wherein the outer periphery of said connector portion is surrounded by said metallic member.

4. An electronic endoscope apparatus according to claim 2, wherein said metallic member comprises a tube which projects from said one of said light source device and said video processor.

5. An electronic endoscope apparatus according to claim 4, wherein said tube is detachable from said one of said light source device and said video processor.

6. An electronic endoscope apparatus according to claim 1, further comprising, within the endoscope insertion portion of said electronic endoscope:

at least a forceps insertion and passage tube; and a light guide bundle and a protection tube for covering and protecting said light guide bundle, wherein said signal cable is arranged substantially at a center of the insertion part, and wherein at least the forceps insertion and passage tube and the protection tube consisting of a shielding member are arranged around said signal cable.

7. An electronic endoscope apparatus according to claim 1, wherein said lead wires provide a double shielding layer, and wherein the lead wires which form respectively the shielding layers have the same winding direction.

8. An electronic endoscope according to claim 7, further comprising:

an insulation layer between the shielding layers which are superposed one upon the other.

9. An electronic endoscope apparatus to claim 7, wherein the different diameters of the lead wires which form said double shielding layer are set in conformance with frequency of generated noises.

* * * * *